United States Patent
Heinonen et al.

(10) Patent No.: US 8,479,731 B2
(45) Date of Patent: Jul. 9, 2013

(54) METHOD AND APPARATUS FOR INDICATING THE ABSENCE OF A PULMONARY EMBOLISM IN A PATIENT

(75) Inventors: Erkki Heinonen, Helsinki (FI); Rene Coffeng, Helsinki (FI); Franck Verschuren, Sterrebeek (BE)

(73) Assignee: General Electric Company, Schenectady, NY (US)

( * ) Notice: Subject to any disclaimer, the term of this patent is extended or adjusted under 35 U.S.C. 154(b) by 1890 days.

(21) Appl. No.: 11/292,957

(22) Filed: Dec. 2, 2005

(65) Prior Publication Data
US 2007/0129646 A1    Jun. 7, 2007

(51) Int. Cl.
| A61M 11/00 | (2006.01) |
| A61M 16/00 | (2006.01) |
| F16K 31/02 | (2006.01) |
| A62B 9/00  | (2006.01) |
| A61B 5/00  | (2006.01) |
| A61B 5/08  | (2006.01) |

(52) U.S. Cl.
USPC ............ 128/204.22; 128/200.26; 128/204.23; 128/200.15; 128/204.21; 128/205.23; 128/920; 600/529; 600/532; 600/301; 600/309; 600/310; 600/322; 600/364

(58) Field of Classification Search
USPC ............. 128/200.26, 204.22, 204.23, 200.15, 128/204.21, 205.23, 920; 600/529, 532, 301, 600/309, 310, 322, 364
See application file for complete search history.

(56) References Cited

U.S. PATENT DOCUMENTS
7,074,196 B2 *   7/2006   Kuck et al. ..................... 600/532
2003/0060727 A1 *   3/2003   Kline ............................. 600/538

OTHER PUBLICATIONS

*The Concept of Deadspace with Special Reference to the Single breath Test for Carbon Dioxide*, R. Fletcher et al., Brit. Journal Anaesth. (1981), vol. 53, pp. 77-88.

* cited by examiner

*Primary Examiner* — Patricia Bianco
*Assistant Examiner* — Nihir Patel
(74) *Attorney, Agent, or Firm* — Andrus, Sceales, Starke & Sawall, LLP

(57) ABSTRACT

A method and apparatus for determining the presence or absence of a pulmonary embolism (PE) in a patient. The breathing gas $CO_2$ partial pressure ($PCO_2$) during the expiration of breathing gases by the patient, the end tidal ($EtCO_2$), $CO_2$ partial pressure, and the $CO_2$ partial pressure ($PaCO_2$) of the blood are measured. The volume (V) of breathing gases expired during the expiration of breathing gases by the patient is also measured and a relationship between changes in breathing gas $CO_2$ partial pressure ($PCO_2$) and changes in breathing gas volume (V) in an alveolar expiration phase of patient expiration is determined. The difference between the blood $CO_2$ partial pressure ($PaCO_2$) and the end expiration $CO_2$ partial pressure is divided by the relationship between $PCO_2$ and V produce a quantity which is compared to a threshold value. If the quantity is below the threshold value, the absence of a pulmonary embolism is indicated.

22 Claims, 2 Drawing Sheets

METHOD AND APPARATUS FOR INDICATING THE ABSENCE OF A PULMONARY EMBOLISM IN A PATIENT

FIELD OF THE INVENTION

The present invention relates to a method and apparatus for indicating an embolic condition of a patient. To this end, the invention may be used to indicate the absence of a pulmonary embolism in a patient.

BACKGROUND OF THE INVENTION

Pulmonary embolism (PE) is a blockage or occlusion of a pulmonary blood vessel. Most commonly it is caused by a blood clot or thrombosis, that is, an "embolus", in a vessel. It is a common illness with an annual incidence of 1 in a 1,000 in the Western world population. Mortality of PE is 30% when left undiagnosed and untreated but with treatment this can be reduced to 5-8%. The diagnosis of PE is difficult and is typically based on multi-step algorithms starting from an evaluation of the clinical probability and laboratory tests for markers, but positive diagnosis always requires some kind of imaging, ventilation-perfusion lung scintigraphy, pulmonary angiography, or multi-detector spiral X-ray computed tomography.

In an emergency department, the prevalence of PE is around 20%, which means that 5 patients are suspects for each case of actual PE. In these circumstances, the incidence of PE suspicion based on clinical probability can be estimated to be 1 in 200 of population. Diagnostic laboratory tests, called D-dimers, have good sensitivity to exclude PE but poor specificity to confirm it. Out of five suspected PE patients, only two are excluded with such diagnostic laboratory tests. Thus, of the remaining three patients, two will be PE negative and one will be an actual case of PE. Imaging these PE patients increases the cost of diagnosing PE. To reduce this cost, non-invasive diagnostic techniques with good sensitivity for excluding PE are needed.

To this end, indices derived from a comparison of expired breathing gas carbon dioxide ($CO_2$) concentration with arterial blood $CO_2$ partial pressure ($PaCO_2$) have been experimented with. One such method plots expired $CO_2$ over expired gas volume. The slope of the alveolar expiration portion of the plotted curve is then extrapolated to an expired gas volume comprising 15% of total lung capacity (TLC). The difference between the $CO_2$ concentration determined by this extrapolation and the $PaCO_2$ should be less than 12% of $PaCO_2$ to exclude the existence of PE. This method suffers a weakness that reduces its diagnostic accuracy: that is, TLC values are statistical parameters determined from a large group of patients and expressed as nomograms for patient sex and size. PE suspected individuals may, however, differ a lot from these averages, which provides a source of error. In the worst case, this may result in false negative diagnosis of PE and a patient that is endangered with the high mortality of untreated PE.

SUMMARY OF THE INVENTON

The present invention relates to the measurement of ventilation and perfusion (V/Q) distribution in the lungs of a patient. More particularly, the present invention relates to identifying the inequalities in ventilation distribution for diagnostic purposes and for obtaining diagnostic conclusions from the result. A diagnostic conclusion includes the absence of PE in the patient.

Alveolar ventilation is gas exchange in the alveoli induced by the sequential filling (inspiration) and emptying (expiration) of the lungs during tidal breathing. The breathing gases provided by ventilation and the blood interact in the alveoli, enabling gas exchange between blood and alveolar gases. The driving force for this gas exchange is differences in gas partial pressures in the blood and in the alveolar gases. This driving force makes oxygen diffuse from alveoli to the blood and carbon dioxide diffuse from the blood to the alveolar gases.

Ideally, ventilation and perfusion distribute to the same regions of the lungs. This is however not always the case, and various mismatches of the distributions exist. The most significant of these distribution inequalities are shunt perfusion (blood perfuses through lung regions that are not ventilated) and dead-spaces (ventilation penetrates to lung regions that are not perfused by blood). Neither of these regions participate in gas exchange. In addition there are regions where perfusion is overweighted in relation to ventilation and vice versa causing impairment of the gas exchange.

Capnography measures breathing gas $CO_2$ concentrations. In routine bedside use, the concentration is measured over time showing a pattern of breathing respiratory cycles divided into inspiration and expiration phases. By combining capnographic measurement during expiration with a spirometric measurement of breath volume, a volumetric capnograph (VCap) may be generated. An advantage of a VCap is that each point on the capnographic curve provides an image of ventilation distribution at different lung regions. Thus, early expiration breathing gas comes from those airways of the lung having practically zero $CO_2$ concentration since they contain inspired breathing gases from a previous inspiration. Gas from the alveolar region then follows. This alveolar gas $CO_2$ concentration is a flow-weighted average of the gas concentrations from different lung regions. The flow rates from different lung regions vary according to variations in local pressure, compliance, and flow resistance. These factors determine the ventilation of the regions of the lung. In addition to this, gas concentration in different alveoli depend on the blood perfusion rate for the alveoli.

Thus, the complicated mixing process occurring in the lungs and the V/Q distribution of the lungs determine the gas concentration during alveolar expiration. This concentration is quantified as the slope of the alveolar expiration portion of the profile of the VCap curve. In a normal lung, the ventilation and perfusion are matched and the alveolar expiration slope is flat. With ventilation disorders, like chronic obstructive pulmonary disease (COPD), high airway resistance reduces regional ventilation and slows down the emptying of the lungs during expiration. Gases from these obstructed regions are overweighted in the end-expiration mixture resulting in a characteristic steeply rising alveolar expiration slope. The slope may be steeply rising also when differences in regional compliance within the lungs exist. The filling of low compliant regions is overweighted at end-inspiration and, respectively, the emptying of these regions is overweighted at early-expiration. Thus, the time available for gas exchange in these low-compliant regions is short, reducing the mixture $CO_2$ concentration at early alveolar expiration.

VCap has been combined with arterial blood $CO_2$ partial pressure ($PaCO_2$) measured from a blood sample with a blood gas analyzer. In an ideal lung without shunt and alveolar dead-space, the end tidal $CO_2$ ($EtCO_2$) is very close to $PaCO_2$. However, with various diseases of the lung or illnesses, the $PaCO_2$–$EtCO_2$ difference increases. As described above, the alveolar expiration slope of the VCap curve may also increase.

In an ideal representation of the occurrence PE in the lungs, ventilation of dead-spaces in the lungs resulting from blood vessel thrombosis (high V/Q) occurs in parallel with the ventilation of normal (V/Q=1) regions. During inspiration, breathing gases penetrate in parallel to both these regions. In the normal V/Q regions, the gases become enriched with $CO_2$, whereas in high V/Q, dead-space regions, the composition of the gases remains unchanged due to the absence of blood perfusion. During expiration, gases are also expired from these regions in parallel. During expiration, gases from the dead-spaces of the lungs dilute the $CO_2$ concentration of the gases from normal V/Q regions. Thus, the characteristic VCap curve of a patient experiencing PE has a flat alveolar expiration slope, but $EtCO_2$ is lowered compared to $PaCO_2$. In contrast to the foregoing, in other illnesses where the $PaCO_2$ to $EtCO_2$ difference also tends to increase, the slope of the VCap curve increases as well, as noted above.

In the present invention, an index for indicating the embolic condition of a patient (a PEindex) is established by determining the ratio of the $PaCO_2$–$EtCO_2$ difference to the alveolar expiration slope of the VCap curve. The alveolar expiration slope is defined as the change in $CO_2$ concentration or partial pressure divided by the change in volume of the expired breathing gases. As will be hereinafter shown, in the determination of the PEindex, the unit for the PEindex will be a volume measurement unit, e.g. milliliters.

The method and apparatus of the invention may be used not only in PE diagnosis but also in monitoring of thrombolysis therapy carried out to eliminate the blood clot(s) causing the embolism.

An advantage of the present invention is that the result relies only on measurements taken from the individual patient for whom the diagnosis is needed, thereby avoiding reliance on population-derived statistical entities that may be totally invalid for a given individual patient.

Another advantage of the invention is that except for the arterial blood sampling, which is a normal clinical routine and particularly in emergency departments, the measurements are non-invasive. Further advantages when considered in the aspect of a PE diagnostic technique are the simplicity and cost-effectiveness of the method and apparatus that contribute to a more effective diagnosis of PE in form of reducing the number of patients requiring expensive imaging procedures.

When used in an emergency department, the intended use of the invention is to exclude the presence of PE. In this role, sensitivity to PE exclusion has to be very close to unity, i.e. no PE positive patients should be deemed as PE negative. This is a challenging task in case of minor peripheral PE where the total effect on the $PaCO_2$–$EtCO_2$ difference is small. If the slope is small as well, PEindex reading will be very sensitive to measurement errors. In such circumstances, the method and apparatus of the invention includes a sensitivity analysis, where the PEindex is determined by taking into consideration the worst case error margin in determination of $PaCO_2$, $EtCO_2$, and alveolar expiration slope.

In terms of avoiding false negatives, the validity of the $PaCO_2$ measurement for comparison with $EtCO_2$ also has to be assured with respect to shunt perfusion. As described above, shunt perfusion in the lung is blood flow through regions of the lung that are not ventilated. Thus the shunted blood has the composition of mixed venous blood. In comparison with the capillary perfusion meeting with ventilation in the lung, the $PCO_2$ of the shunted blood is high and the $PO_2$ low due to the lack of gas exchange. Differences in $PCO_2$ between the two types of blood perfusion is however small.

Ideally for the purpose of PE diagnosis, $EtCO_2$ should be compared with the capillary blood $PCO_2$. However this is not possible and the arterial blood used in the present invention is a mixture of the shunt and capillary perfusions. Thus, primary effect of the shunt perfusion is slight increase of $PaCO_2$ but a more significant reduction of $PaO_2$ as compared to the capillary blood.

Blood $PCO_2$ also is sensitive to blood $PO_2$. The lower the $PO_2$, the higher the blood carbamino $CO_2$ capacity. This is called as Halldane effect. As a result of this effect, the lowed $PO_2$ of the arterial blood when shunt perfusion is present also reduces the $PCO_2$ when dissolved $CO_2$ forming the $PCO_2$ becomes bound to carbamino compounds. The net effect of the shunt perfusion may be that the $PaCO_2$ may be lower than the ideal $PCO_2$ of the capillary blood. Comparing the lowered $PaCO_2$ with $ETCO_2$ will thus give a lower PE index value, which may result in false PE exclusion, i.e. an indication that PE is not present when it in fact, is present.

A high $PaO_2$–$EtO_2$ difference indicates the presence of shunt perfusion due to the lowered oxygen level in the blood. Therefore, patients with high $O_2$ difference either are excluded from the analysis and deemed potentially positive PE patients, or alternatively, the $PaCO_2$ is compensated for the $PCO_2$ of capillary blood.

The present invention will be further appreciated from the following detailed description taken in conjunction with the accompanying drawing.

DETAILED DESCRIPTION

Figure 1:
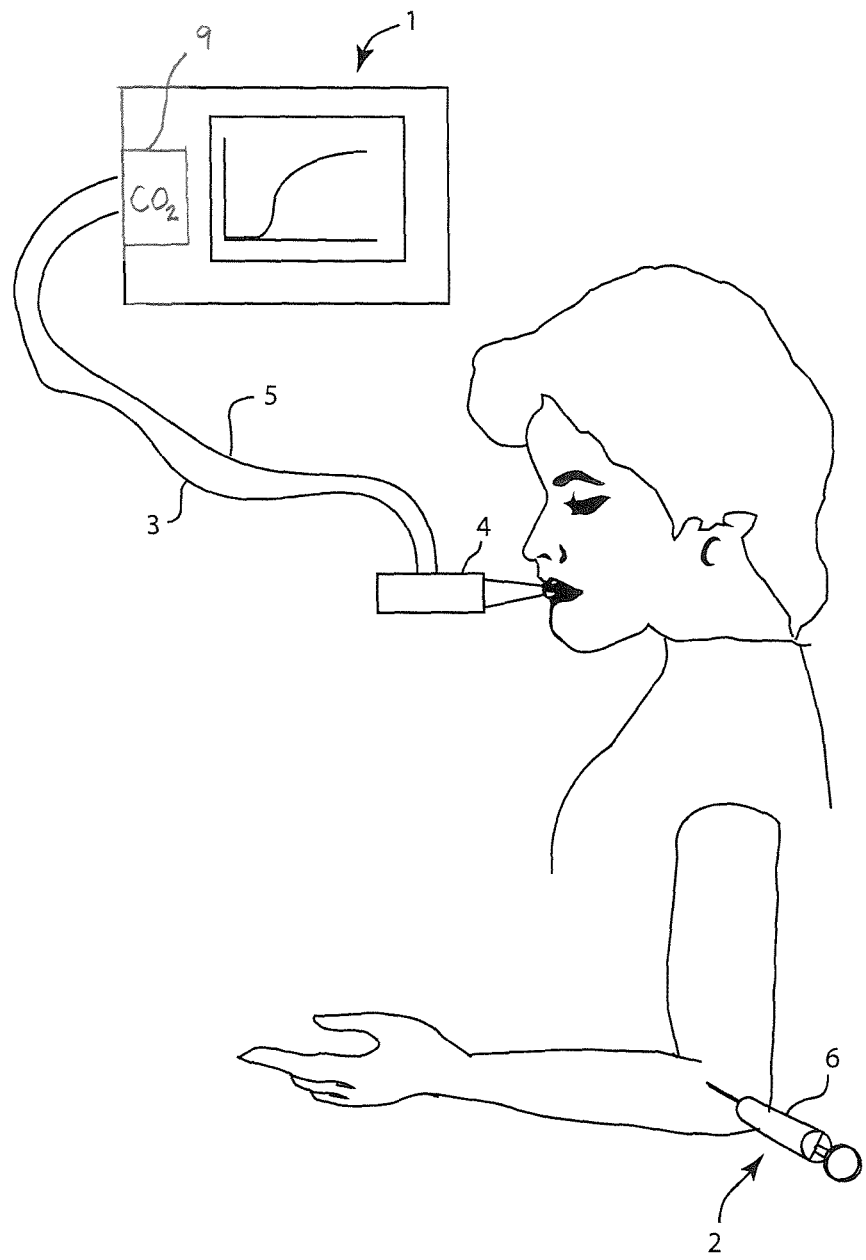
FIG. 1 shows apparatus of the present invention and a manner of making the measurements employed in the method of the present invention.

FIG. 1 shows VCap measurement apparatus 1 and arterial blood sampling apparatus 2. Apparatus 1 includes an expired breathing gas $CO_2$ concentration sensor 9, which is advantageously an infrared gas analyzer. Such analyzer may be either of a mainstream type, in which the infrared absorption path is directly at the breathing gas pathway, or alternatively of a sidestream type, in which a sample of the breathing gas is withdrawn with a sampling line 3 transporting a sample flow of the breathing gas to the infrared absorption path of the sensor for measurement.

Breathing gas volume may be measured advantageously with any type of well-known flow sensor 4, based on pressure difference measurement over a known flow restrictor, a thermal sensor, an ultrasound sensor, or other suitable sensor. Flow sensor 4 is coupled to apparatus 1 by conductor 5. The volume is determined by integration of the flow signal with respect to time. If the gas concentration is determined with sidestream technology, the gas measurement and volume measurement signals need to be synchronized to account for the sample gas transport delay. With a mainstream gas sensor the signals are inherently synchronized since no gas transport is needed.

To allow comparison of the breathing gases composition with blood gas partial pressures, breathing is advantageously recorded at the same time that the arterial blood is sampled in a syringe 6 from an artery of the patient. Arterial blood sampling is a standard clinical procedure with the blood gas quantities in the sample being determined in a blood gas analyzer (not shown).

Figure 2:
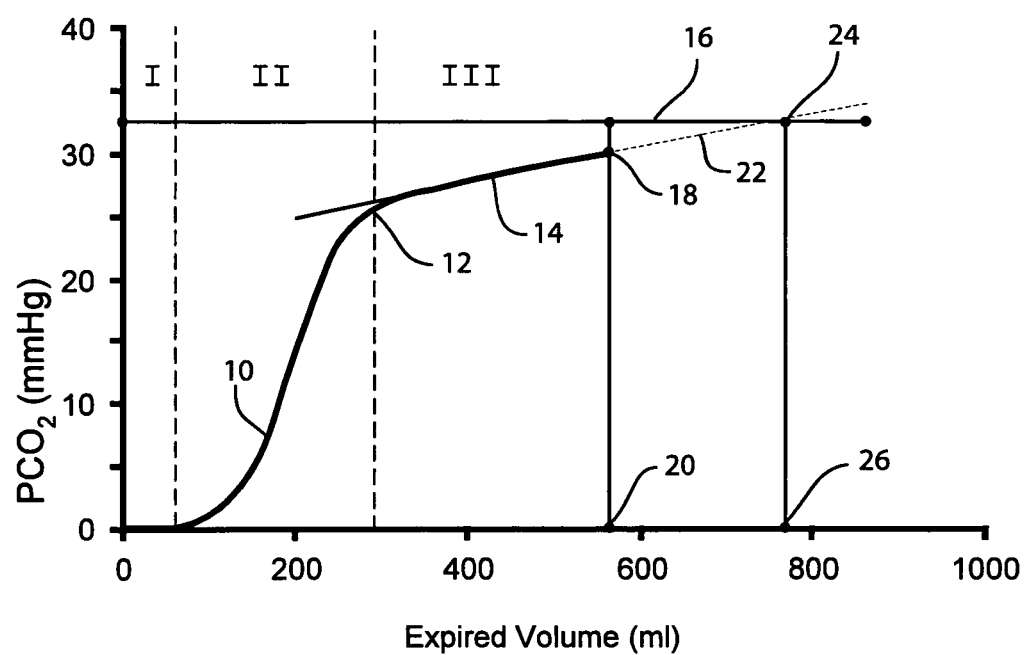
FIG. 2 is a graph showing a VCap curve and the determination of the PEindex.

The volumetric capnograph VCap plot or curve shown in FIG. 2 presents $CO_2$ partial pressure in millimeters of mercury (mmHg) on the ordinate as a function of expiration breathing gas volume in milliliters (ml) on the abscissa for an exhalation phase of the breath cycle as presented by Fletcher (British J Anesth (1981), 53, 77-88). The VCap curve is divided into three sectors enumerated as I-III. The number I denominates the expiration of breathing gases from the anatomical dead space of the patient. This is $CO_2$-free inspiration gas remaining in the airways at the end of inspiration that is exhaled at the beginning of expiration. Alternatively, this is often called also airway- or serial dead space. Following this, a transitional phase denominated by the number II represents the phase in which the anatomic dead space expiration transforms to alveolar expiration. The slope of the transitional expiration curve portion 10 is determined from the expiration points of the VCap curve in sector II.

The beginning of the alveolar expiration phase and of sector III in the graph of FIG. 2 may be nominated as the point 12 at which the slope of the VCap curve portion 14 is reduced to a predetermined percentage of the maximum slope determined during the transition phase of sector II. 15% has been observed as a good value for the denomination, although the method is not limited to this limit. It could be as well 10% or 20% without a major effect on the outcome of the technique.

Alternatively, the alveolar expiration phase in which slope is determined could be simply e.g. the last 10%, 15%, or 20% of the expiration volume. Also any combination of these criteria could be used. Such combination would assure the minimum percentage of the concluding expiration volume to be used for determining the slope in case the slope of the VCap curve does not reach the reduction criteria, or reaches the reduction criteria close to the end of expiration Shallow breathing by the patient may present a problem in VCap analysis. In such a breathing pattern, a useful alveolar slope reduction, such as that shown as 14 in FIG. 2, may not be reached at all. Inability to meet the slope reduction criteria described above could be used as criteria to invalidate the VCap measurement in PE diagnosis to avoid possible false negative diagnosis.

Arterial $CO_2$ partial pressure ($PaCO_2$) is also used with the VCap measurement and curve plot to determine the presence of PE. A measurement of $PaCO_2$ is shown as a horizontal line 16 intersecting with the ordinate of FIG. 2 at the value of the arterial $CO_2$ partial pressure ($PaCO_2$). End tidal $CO_2$ ($EtCO_2$) is the VCap curve end point 18 value as measured at the ordinate of the graph of FIG. 2. Thus, the $PaCO_2$-$EtCO_2$ difference is the vertical distance from the VCap curve endpoint 18 to the $PaCO_2$ line 16 on the ordinate of the graph of FIG. 2. In the example of FIG. 2, the difference is about 3 mmHg. The respective value 20 on the abscissa for the end of expiration is the breath tidal volume (VT). In the example shown, the tidal volume is about 575 ml.

An extrapolation of the slope line of the alveolar expiration portion 14 of the VCap curve toward increasing gas volume is presented in FIG. 2 with dotted line 22. This line intersects the $PaCO_2$ line 16 at point 24. The horizontal difference from point 24 at the abscissa, that is, point 26, to the tidal volume VT point 20 at the abscissa gives a graphical presentation of the PEindex. In the case illustrated in FIG. 2, the PEindex is exemplarily shown as approximately 200 ml. A typical threshold value for PEindex is currently seen as 250 mL, more generally between 200 mL and 300 mL. To exclude the presence of PE in a patient, the value of the PEindex must be less than the threshold value.

The algebraic presentation for the difference, and hence for the index is $$PEindex = \frac{PaCO_2 - EtCO_2}{slope}$$

with slope being that of lines 14 and 22. In normally ventilated patients the slope is typically 0.03 mmHg/mL. However, values of 0.01 mmhg/mL are frequently found, but a slope below 0.005 mmHg/mL is rare.

While the present invention has been described as indicating the absence of PE in a patient, it will be appreciated that should the PEindex value exceed the threshold value, it may be seen as an indication of the presence of PE in a patient. Further, it is to be understood that the indications provided by the present invention are not infallible and the certainty of the absence or presence of PE, while currently seen as high, is to be understood to be of a nature to be medically useful.

The sensitivity of the PEindex to the $CO_2$ partial pressure difference can be expressed through derivation as $$d(PEindex) = \frac{d(PaCO_2 - EtCO_2)}{slope}$$

To exclude a diagnosis of PE when none, in fact, exists, the PEindex has to be below threshold limit less a margin of error, i.e.

$$\frac{(PaCO_2 - EtCO_2)}{slope} < threshold - \left(\frac{d(PaCO_2 - EtCO_2)}{slope}\right)$$

The effect of the error margin becomes more dominant, as the slope becomes less. For example, the error margin for a $CO_2$ pressure difference of 1 mmHg and a slope 0.05 mmHg/mL is 20 ml. whereas for a slope of 0.01 mmHg/mL, the error margin will be 100 mL.

To avoid false PE exclusion due to shunt perfusion, apparatus 1 may include an oxygen sensor for sensing $EtO_2$. The analysis of the gases in the arterial blood sample taken from the patient includes $PaO_2$. Patients with a high difference between $EtO_2$ and $PaO_2$ may be excluded from diagnosis using the PEindex and deemed potentially PE positive.

Alternatively, the $PaCO_2$ may be compensated for the Haldane effect caused by the shunt perfusion. This may be done by the following alteration to the blood $CO_2$ quantity $$PCO_2(capillary) = k*((EtO_2 - PaO_2) - c) + PaCO_2$$

where the factor k is the carbamino capacity sensitivity on $PO_2$ gain factor and c is normal difference between capillary blood $PO_2$ and $EtO_2$. An observed value for k is typically 0.04 and for c 20 mmHg.

The PEindex can be used to monitor the efficacy of PE thrombolysis therapy. In this application the measurement can be repeated periodically during and after the therapy and comparing subsequent results to an initial value recorded before thrombolysis therapy reveals the therapeutic effect of the treatment.

Various alternatives and embodiments are contemplated as being within the scope of the following claims particularly pointing out and distinctly claiming the subject matter regarded as the invention.

What is claimed is:

1. A method for determining the presence or absence of a pulmonary embolism in a patient, said method comprising the steps of:

(a) measuring the amount of $CO_2$ expired by the patient during the expiration of breathing gases by the patient using a breathing gas $CO_2$ concentration sensor;

(b) measuring the volume (V) of breathing gases expired during the expiration of breathing gases by the patient using a flow sensor;

(c) determining a slope in a measurement apparatus, the slope defined by a change in the amount of expired $CO_2$ divided by a change in breathing gas volume in an alveolar expiration phase of patient expiration;

(d) measuring an amount of $CO_2$ in the lungs of the patient at the end of expiration using the breathing gas $CO_2$ concentration sensor;

(e) measuring the amount of $CO_2$ in the blood of the patient;

(f) determining the difference in the measurement apparatus between the amount of $CO_2$ in the blood and the amount of $CO_2$ in the lungs of the patient at the end of expiration;

(g) establishing a relationship in the measurement apparatus between the determination of step (f) and the determination of step (c) to produce a quantity for use in determining the presence or absence of a pulmonary embolism in the patient, and (h) defining the alveolar expiration phase of patient expiration as that in which the quantity produced in step (c) is reduced to a given percentage of a corresponding quantity produced for a previous phase of expiration.

2. The method according to claim 1 further including a step of establishing a threshold value for the quantity produced in step (g) and indicating the presence or absence of a pulmonary embolism by the relationship of the quantity to the threshold value.

3. The method according to claim 2 further defined as indicating the presence of a pulmonary embolism when the quantity produced in step (g) is below the threshold value.

4. The method according to claim 3 wherein the threshold value is expressed in milliliters and wherein the threshold value is 250 mL or greater.

5. The method according to claim 4 wherein the threshold value is between 250 and 300 mL.

6. The method according to claim 3 wherein an indication of the absence of PE is made when the quantity produced in step (g) is below a quantity comprising the threshold value less a margin of error.

7. The method according to claim 1 wherein step (g) is further defined as dividing the determination of step (f) by the determination of step (c) to produce the quantity.

8. The method according to claim 7 further including a step of establishing a threshold value for the quantity produced in step (g) and indicating the presence or absence of a pulmonary embolism by the relationship of the quantity to the threshold value.

9. The method according to claim 8 further defined as indicating the presence of a pulmonary embolism when the quantity produced in step (g) is below the threshold value.

10. The method according to claim 9 wherein the threshold value is expressed in milliliters and wherein the threshold value is 250 mL or greater.

11. The method according to claim 10 wherein the threshold value is between 250 and 300 mL.

12. The method according to claim 9 wherein an indication of the absence of PE is made when the quantity produced in step (g) is below a quantity comprising the threshold value less a margin of error.

13. The method according to claim 1 wherein the measurements of $CO_2$ amounts are expressed as $CO_2$ partial pressures.

14. The method according to claim 13 wherein step (d) is further defined as measuring the $CO_2$ partial pressure of the breathing gases of the patient at the end of expiration.

15. The method according to claim 13 wherein the measurement of $CO_2$ in step (e) is arterial blood $CO_2$ ($PaCO_2$).

16. The method according to claim 15 wherein the measurement of $CO_2$ in the arterial blood of the patient is compensated for the effect of shunt perfusion in the lungs of the subject.

17. The method according to claim 1 wherein the step of defining the alveolar expiration phase is further defined as defining the alveolar expiration phase as that in which the quantity produced in step (c) is 10-20% of the corresponding quantity produced for the previous phase of expiration.

18. The method according to claim 17 wherein the step of defining the alveolar expiration phase is further defined as defining the alveolar expiration phase as that in which the quantity produced in step (g) is 15% of the corresponding quantity produced for the previous expiration phase.

19. The method of claim 1 wherein the step of defining the alveolar expiration phase is further defined as using a combination of criteria relating to the quantity produced in step (c) and to the expiration volume.

20. The method according to claim 1 further including the step of preventing a determination of PE diagnosis if the quantity produced in step (c) does not meet a magnitude reduction criterion.

21. A method for determining the presence or absence of a pulmonary embolism in a patient, said method comprising the steps of:

(a) measuring the amount of $CO_2$ expired by the patient during the expiration of breathing gases by the patient using a breathing gas $CO_2$ concentration sensor;

(b) measuring the volume (V) of breathing gases expired during the expiration of breathing gases by the patient using a flow sensor;

(c) determining a slope in a measurement apparatus, the slope defined by a change in the amount of expired $CO_2$ divided by a change in breathing gas volume in an alveolar expiration phase of patient expiration;

(d) measuring an amount of $CO_2$ in the lungs of the patient at the end of expiration using the breathing gas $CO_2$ concentration sensor;

(e) measuring the amount of $CO_2$ in the blood of the patient;

(f) determining the difference in the measurement apparatus between the amount of $CO_2$ in the blood and the amount of $CO_2$ in the lungs of the patient at the end of expiration;

(g) establishing a relationship in the measurement apparatus between the determination of step (f) and the determination of step (c) to produce a quantity for use in determining the presence or absence of a pulmonary embolism in the patient; and (h) defining the alveolar expiration phase as the concluding 10%-20% of the expiration volume.

22. A method for determining the presence or absence of a pulmonary embolism in a patient, said method comprising the steps of:

(a) measuring the amount of $CO_2$ expired by the patient during the expiration of breathing gases by the patient using a breathing gas $CO_2$ concentration sensor;

(b) measuring the volume (V) of breathing gases expired during the expiration of breathing gases by the patient using a flow sensor;

(c) determining a slope in a measurement apparatus, the slope defined by a change in the amount of expired $CO_2$ divided by a change in breathing gas volume in an alveolar expiration phase of patient expiration;
(d) measuring an amount of $CO_2$ in the lungs of the patient at the end of expiration using the breathing gas $CO_2$ concentration sensor;
(e) measuring the amount of $CO_2$ in the blood of the patient;
(f) determining the difference in the measurement apparatus between the amount of $CO_2$ in the blood and the amount of $CO_2$ in the lungs of the patient at the end of expiration;
(g) establishing a relationship in the measurement apparatus between the determination of step (f) and the determination of step (c) to produce a quantity for use in determining the presence or absence of a pulmonary embolism in the patient;
(h) measuring the $O_2$ partial pressure ($EtO_2$) of the breathing gases at the end of expiration;
(i) measuring the $O_2$ partial pressure ($PaO_2$) in the blood of the patient;
(j) comparing $EtO_2$ and $PaO_2$; and
(k) precluding an indication of the absence of a pulmonary embolism if the $O_2$ difference exceeds a predetermined value.

* * * * *